(12) United States Patent
Katsnelson

(10) Patent No.: US 10,016,489 B2
(45) Date of Patent: Jul. 10, 2018

(54) METHODS AND COMPOSITIONS FOR TREATING DISEASES

(71) Applicant: NIZYME, INC., San Francisco, CA (US)

(72) Inventor: Ilana Katsnelson, San Francisco, CA (US)

( * ) Notice: Subject to any disclaimer, the term of this patent is extended or adjusted under 35 U.S.C. 154(b) by 152 days.

(21) Appl. No.: 15/103,280

(22) PCT Filed: Apr. 23, 2014

(86) PCT No.: PCT/US2014/035093
§ 371 (c)(1),
(2) Date: Jun. 9, 2016

(87) PCT Pub. No.: WO2014/176309
PCT Pub. Date: Oct. 30, 2014

(65) Prior Publication Data
US 2016/0310579 A1    Oct. 27, 2016

Related U.S. Application Data

(60) Provisional application No. 61/815,206, filed on Apr. 23, 2013.

(51) Int. Cl.
*A61K 38/44* (2006.01)
*A61K 31/145* (2006.01)
*A61K 47/48* (2006.01)

(52) U.S. Cl.
CPC ............ *A61K 38/44* (2013.01); *A61K 31/145* (2013.01); *A61K 47/48215* (2013.01); *C12Y 102/01003* (2013.01)

(58) Field of Classification Search
CPC .......... A61K 2300/00; A23V 2200/334; C12Y 102/01003
See application file for complete search history.

(56) References Cited

U.S. PATENT DOCUMENTS

| | | | | |
|---|---|---|---|---|
| 4,678,809 A | * | 7/1987 | Phillips | A61K 9/0019 424/486 |
| 5,855,881 A | * | 1/1999 | Loike | C12Y 101/01001 424/94.2 |
| 2010/0113423 A1 | * | 5/2010 | Mochly-Rosen | C07C 233/29 514/217.11 |

OTHER PUBLICATIONS

Roberts et al. Chemistry for peptide and protein PEGylation. Advanced Drug Delivery Reviews. 2002;54:459-476.*

* cited by examiner

*Primary Examiner* — Lynn Y Fan
(74) *Attorney, Agent, or Firm* — Gary Baker; BioPatent

(57) ABSTRACT

The present invention provides methods and compositions comprising ALDH2 in the treatment of a patient with toxicity resulting from ALDH2 deficiency. The physiological states that may be treated using the present invention include temporary ALDH2 deficiency, such as that seen by alcohol poisoning or an ischemic event.

20 Claims, 4 Drawing Sheets

METHODS AND COMPOSITIONS FOR TREATING DISEASES

CROSS-REFERENCE TO RELATED APPLICATIONS

This application claims the priority benefit of PCT/US2014/035,093, filed Apr. 23, 2014, entitled "METHODS AND COMPOSITIONS FOR TREATING DISEASES", and U.S. Provisional Patent Application Ser. No. 61/815,206, filed Apr. 23, 2013, of which the full disclosure of these applications, are incorporated herein by reference for all purposes.

FIELD OF THE INVENTION

This invention relates to methods and compositions for the treatment of physiological conditions associated with acetaldehyde dehydrogenase 2 (ALDH2) deficiencies.

BACKGROUND OF THE INVENTION

In the following discussion certain articles and processes will be described for background and introductory purposes. Nothing contained herein is to be construed as an "admission" of prior art. Applicant expressly reserves the right to demonstrate, where appropriate, that the articles and processes referenced herein do not constitute prior art under the applicable statutory provisions.

Alcohol poisoning occurs when a patient drinks a very large amount of alcohol (ethanol) during a short period of time. Very large doses of alcohol cause saturation of the enzymes involved in metabolism of alcohol, thus allowing only a fraction of the alcohol to be converted by metabolic transformation to its non-toxic end product (zero-order kinetics for drug metabolism).

Disulfiram (Antabuse™) is a drug that is used to treat both alcohol and cocaine dependencies. Its mechanism of action is inhibition of the enzyme ALDH2 resulting in accumulation of acetaldehyde and symptoms of acetaldehyde poisoning (or alcohol-disulfiram reaction) after consumption of alcohol. Disulfiram was approved for treatment of alcoholism more than 50 years ago, and was initially used as an implant resulting in 100% sobriety. It also caused multiple deaths from alcohol-disulfiram reaction (acetaldehyde poisoning). To avoid deaths and disulfiram toxicity, disulfiram is now administered orally and dose of the drug decreased from 3,000 mg a day to 250 mg a day.

However, this new dosage regime results in reduced overall compliance, as a patient can stop medication and relapse without severe effects. Thus, although current standard of care using oral disulfiram decreases the number of drinking days, it does not ensure abstinence as effectively as an implant (Hughes J C and Cook C C, *Addiction* 1997 April; 92(4):381-95).

Treatment to reverse the alcohol-disulfiram reaction would allow development of a new generation of long-term disulfiram delivery options without fear of fatalities currently associated with such delivery. The present methods and compositions address this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present invention provides methods and compositions comprising ALDH2 in the treatment of a patient with toxicity resulting from ALDH2 deficiency. The physiological states that may be treated using the present invention include temporary ALDH2 deficiency, such as that seen by alcohol poisoning, or genetic ALDH2 deficiency, as is common in certain ethnic populations, More specifically, the invention provides a method of treating toxicity associated with an ALDH2 deficiency in a subject comprising administering ALDH2 or a composition comprising ALDH2 in a therapeutically effective dosage, wherein the dosage results in at least a 25% reduction of the systemic level of toxic chemicals in the subject. More preferably the dosage results in at least a 35% reduction of the systemic level of toxic chemicals in the subject, and even more preferably the dosage results in at least a 50% reduction of the systemic level of toxic chemicals in the subject.

In certain embodiments, the toxic chemical measured is the toxic chemical causing the toxicity, e.g., alcohol or cocaine. In other embodiments, the toxic chemical measured is a metabolic by-product of a pharmacologically active substance, e.g., a toxic aldehyde resulting from the metabolism of alcohol.

In yet other embodiments, the toxic chemical measured is a toxic aldehyde created as a physiological response, e.g., toxic aldehydes resulting from ischemic The subject treated may have a temporary ALDH2 deficiency. e.g., that caused by a pharmacologically active substance or injury. The subject may also have a permanent genetic ALDH2 deficiency.

In one specific embodiment, ALDH2 or a composition comprising ALDH2 is administered to a patient exhibiting toxicity due to an acute, temporary ALDH2 deficiency. Commonly, this is caused by ingestion of an amount of a pharmacologically active substance (e.g., alcohol) that overwhelms the natural levels of ALDH2 available for metabolism of that substance. For such patients, this physiological state is temporary, and thus addressing the temporary deficiency may prevent the toxicity otherwise seen and prevent serious organ damage or even death.

The invention provides a method of treating toxicity associated with an ALDH2 deficiency in a subject under the influence of a pharmacologically active substance, comprising administering ALDH2 or a composition comprising ALDH2 in an amount sufficient to restore first order kinetics of the pharmacologically active substance. In some embodiments, the pharmacologically active substance is alcohol. In related embodiments, the subjects being treated have been administered disulfiram, and thus are more prone to the toxic effects of the pharmacologically active substance due to reduced levels of ALDH2.

The methods of the invention may be particularly useful in a patients undergoing treatment for addiction (e.g., addiction to alcohol or cocaine) involving administration of disulfiram. The methods can be used as an adjunctive therapy to disulfiram administration, to prevent the potentially lethal effects that may be seen during a relapse. The methods of the invention enable treatments regimes in which the disulfiram is delivered using a controlled release dosage format, e.g., an implantable device.

Temporary ALDH2 deficiency may also occur during ischemia-reperfusion injury, resulting in an accumulation of toxic aldehydes and increased size of organ damage. Administration of ALDH2 or a composition comprising ALDH2 following such an injury, and preferably immediately following such an injury, can neutralize the toxic aldehydes and reduce their damaging effects.

Thus, in another embodiment, the invention provides a method of treating toxicity associated with an ALDH2 deficiency in a subject that has undergone an ischemic event.

In another embodiment, the methods of the invention can be used for treatment of individuals with permanent ALDH2 deficiency, e.g., following the consumption of pharmacologically active substance (e.g., alcohol).

In the above-described methods, preferably, the ALDH2 or composition comprising ALDH2 is administered to a subject in a therapeutically effective dosage from 0.001 g per kg body weight to 5 g per kg body weight. More preferably ALDH2 or a composition comprising ALDH2 is administered to a subject in a therapeutically effective dosage from 0.1 g per kg body weight to 2 g per kg body weight. The therapeutically effective dosage will reduce the systemic level of toxic chemicals (e.g., a pharmacologically active substance or a toxic metabolic by-product of a substance) by at least 25% following administration, more preferably by at least 35% reduction following administration, and more preferably by at least 50% reduction measurable within 2-24 hours following, administration 12 h.

In one embodiment, ALDH2 or a composition comprising ALDH2 is administered to a patient exhibiting toxicity due to an acute, temporary ALDH2 deficiency. Commonly, this is caused by ingestion of an amount of a pharmacologically active substance (e.g., alcohol) that overwhelms the natural levels of ALDH2 available for metabolism of that substance. For such patients, this physiological state is temporary, and thus addressing the temporary deficiency may prevent the toxicity otherwise seen and prevent serious organ damage or even death.

In another embodiment, ALDH2 or a composition comprising ALDH2 is administered to a patient undergoing treatment with addiction following ALDH2 deficiency caused by an interaction of the drug disulfiram with another drug, e.g., alcohol or cocaine. The methods and compositions of the invention can be used to prevent or reduce the effects of disulfiram following a relapse.

Thus, in one embodiment, the present invention relates to methods and compositions to treat addiction, e.g., alcohol or cocaine addiction. The methods of the invention are especially as part of a comprehensive treatment of addiction treatment that would increase abstinence but not be associated with fatalities.

In one example, the methods of the invention can be used in a treatment re e for addiction, e.g., alcohol or cocaine addition, as an adjunct to disulfiram therapy.

In another example, the methods of the invention can be used in a treatment regime for cocaine addiction in conjunction with disulfiram.

In another example, the methods of the invention can be used to treat acute alcohol poisoning.

The invention also provides a composition for use in treating toxicity resulting from an ALDH2 deficiency, the composition comprising ALDH2 and a pharmaceutically suitable carrier. The composition preferably comprises recombinant human ALDH2, and optionally comprises an active agent other than ALDH2 that is useful in treating the condition associated with the ALDH2 deficiency.

One advantage of the invention is that administration of ALDH2 or a composition comprising ALDH2 reduces or eliminates the toxicity associated with ALDH2 deficiency in a patient suffering acute temporary ALDH2 deficiency.

An advantage of the invention is that he long-term disulfiram delivery options enabled using the methods of the invention would reinstate long-term disulfiram delivery as a very effective treatment option for patients with alcoholism or cocaine addiction.

These and other objects, advantages, and features of the invention will become apparent to those persons skilled in the art upon reading the details of the molecules as more fully described below

DETAILED DESCRIPTION OF THE INVENTION

Figure 1:
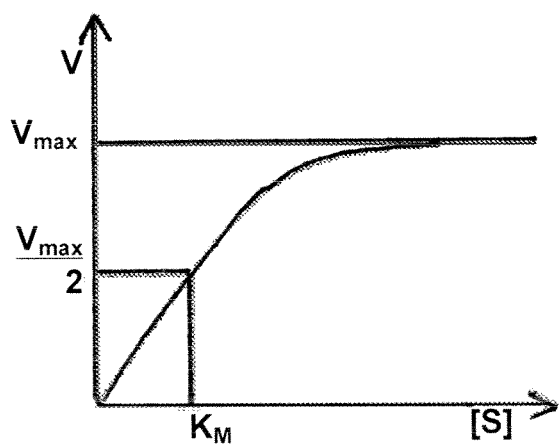
FIG. 1 is a graph showing the effect of drug dose on the rate of metabolism

The exemplary embodiments set forth herein relate to estimating the contribution of cell free nucleic acids from a major source and/or a minor source in a mixed sample. The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular processes and systems provided in particular implementations. However, the processes and systems will operate effectively in other implementations. Phrases such as "exemplary embodiment", "one embodiment and another embodiment" may refer to the same or different embodiments. The embodiments will be described with respect to methods and compositions having certain components. However, the methods and compositions may include more or less components than those shown, and variations in the arrangement and type of the components may be made without departing from the scope of the invention.

The exemplary embodiments will also be described in the context of methods having certain steps. However, the methods and compositions operate effectively with additional steps and steps in different orders that are not inconsistent with the exemplary embodiments. Thus, the present invention is not intended to be limited to the embodiments shown, but is to be accorded the widest scope consistent with the principles and features described herein and as limited only by appended claims.

It should be noted that as used herein and in the appended claims, the singular forms "a," "and," and "the" include plural referents unless the context clearly dictates otherwise. Thus, for example, reference to the effect of "a drug" refers to the effect of one or a combination of drugs, and reference to "a method" includes reference to equivalent steps and processes known to those skilled in the art, and so forth.

Where a range of values is provided, it is to be understood that each intervening value between the upper and lower limit of that range—and any other stated or intervening value in that stated range—is encompassed within the invention. Where the stated range includes upper and lower limits, ranges excluding either of those limits are also included in the invention.

Unless expressly stated, the terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated. All publications mentioned herein are incorporated by reference for the purpose of describing and disclosing the formulations and processes that are described in the publication and which might be used in connection with the presently described invention.

Definitions

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

The terms "Aldehyde dehydrogenase" or "ALDH" as used interchangeably herein refers to all or a pharmacologically active form or fragment of any ALDH molecule, including ALDH1 and ALDH2.

The terms "Aldehyde dehydrogenase 2" or "ALDH2" as used interchangeably herein refers to all or a pharmacologically active form or fragment of the ALDH2 molecule. The ALDH2 may be isolated from a biological source, synthesized or preferably is made using recombinant means. More preferably, the ALDH2 comprises the sequence and structure of human ALDH2. The ALDH2 for use in the present invention may be modified, e.g., to allow tracking of the molecule following administration or to affect the stability of the molecule either before or following administration. The sequence may also be modified to contain certain conserved changes to the protein sequence that allow the molecule to retain its structure and function.

The term "isolated" shall mean separated away from its natural environment. An isolated protein is not necessarily separated away from all materials it is normally present with and may remain associated with certain elements.

The terms "modify", "modification" or "modified" in reference to a protein such as ALDH2 refer to a protein which is altered or derivitized, for example by attachment, linkage, conjugation or complexing with other chemical moieties, by post-translational modification techniques, or by substitution of amino acids.

The terms "PEGylated ALDH2" or "PEG-ALDH2" as used herein refer o an ALDH2 molecule comprising one or more linked PEG molecules.

The terms "treatment", "treating" and "treat" and the like are used herein to generally mean obtaining a desired pharmacological and/or physiological effect. The effect may be prophylactic in terms of completely or partially preventing the toxicity associated with an ALDH2 deficiency or symptom thereof and/or may he therapeutic in terms of partially or completely reducing the adverse effects attributable to ALDH2 deficiency. The "treatment" as used herein covers any treatment of a disease in a mammal, particularly a human.

The Invention in General

This invention provides methods, compositions and devices for treatment of physiological conditions associated with enzyme deficiencies, and in particular temporary enzyme deficiencies. The use of ALDH2 to battle the effects of a deficiency, whether temporary or permanent, allows the treatment of various physiological conditions and the associated toxicity resulting from such a deficiency.

In the case of alcohol poisoning and alcohol-disulfiram reaction, the administration of ALDH2 or a composition comprising ALDH2 would be a very effective treatment to overcome temporary enzyme deficiency. Successful treatment for alcohol-disulfiram reaction would allow for development of a disulfiram-device combination. Development of this type of device is not possible without undressing safety issues associated with a possibly fatal alcohol-disulfiram reaction.

Temporal ALDH2 enzyme deficiency may also occur as a result of ischemia-reperfusion injury, and administration of ALDH2 or a composition comprising ALDH2 may be beneficial in this patient population as well. The present invention is efficacious in treating events associated with drug use and/or addiction, as the administration of ALDH2 or a composition comprising ALDH2 decreases the toxic level of the drug and end-organ damage associated with it.

ALDH2 enzyme therapy is an effective treatment for alcohol-disulfiram reaction. This reaction occurs when a patient who takes disulfiram consumes alcohol. Disulfiram is non-competitive inhibitor of ALDH2 so it creates an "artificial" deficiency of this enzyme. Treatment of severe alcohol-disulfiram reaction would significantly increase safety of disulfiram. Some other drugs (sulfonylureas, quinacrine, griseofuvin, chloramphenicol and others) can also inhibit this enzyme resulting in disultiram like reaction when patients drink alcohol. Human recombinant ALDH2 could also be an effective treatment for disultiram like reaction as well.

Modification of ALDH2

A major challenge for the therapeutic use of many peptides and proteins is their short circulatory half-life. Thus, in certain embodiments of the invention, it is desirable to modify the ALDH molecule to improve its therapeutic properties. For example, conjugation of a therapeutic protein or peptide sequence with biodegradable polymer can prolong the maintenance of therapeutic drug levels relative to administration of the drug itself. Sustained release may be extended up to several weeks depending on the formulation and the active ingredient conjugated. It will be appreciated that modification as herein described preferably occurs without a substantial loss-of-function or biological activity as compared to the function or biological activity of the unmodified ALDH2 protein.

One preferred chemical moiety for modification of ALDH2 is polyethylene glycol (PEG). PEGylation may significantly improve the physicochemical properties (solubility and stability) of biopharmaceuticals such as ALDH2 while also increasing in vivo circulation half-life, e.g., by decreased enzymatic degradation and/or decreased kidney clearance. PEG conveys to molecules such as proteins its physicochemical properties and therefore modifies also biodistribution and solubility of protein-based biopharmaceuticals. More particularly, PEG conjugation may mask a protein's surface and increase the molecular size of the protein, thus reducing its renal ultrafiltration, preventing the approach of antibodies or antigen processing cells and reducing degradation by proteolytic enzymes.

Modification by PEGylation may occur at random positions or a predetermined position within ALDH2, and may include one, two, three or more attached PEG molecules as described herein. There are several methodologies available for protein PEGylation, and conjugation chemistries. Reference is made to Roberts et al (2002) Advanced Drug Delivery Reviews 54: 459-476 and Zalipsky (1995) Advanced Drug Reviews 16: 157-182, and US Pub No 2011/0196134, which provide non-limiting examples of several methodologies available for protein PEGylation, and conjugation chemistries and are incorporated herein by reference.

In order to avoid heterogeneous products resulting from random PEGylation, different strategies have been developed for site-specific PEGylation of proteins, by a combination of site-specific mutagenesis and residue-specific chemical reaction. A method is selective thiol PEGylation targeting free cysteine residues. This strategy has been successfully used for site-directed.

PEG may have a branched or unbranched structure. Non-limiting examples of branched PEGs suitable for conjugation to ALDH2 are provided in U.S. Pat. No. 5,643,575. In particularly preferred embodiments, the PEG is a branched structure.

The PEG molecule suited for use in the present invention may be of any molecular weight between about 1 kDa to about 100 kDa, as practically desired. Typically, although not exclusively, PEG preparations exist as a heterogeneous mixture of PEG molecules either above or below the stated molecular weight. By way of example, the PEG may have an average molecular weight of about 1000, 1500, 2000, 2500, 3000, 3500, 4000, 4500, 5000, 5500, 6000, 6500, 7000, 7500, 8000, 8500, 9000. 9500, 10000, 10500, 11000, 11500, 12000, 12500, 13000, 13500, 14000, 14500, 15000, 15500, 16000, 16500, 17000, 17500, 18000, 18500, 19000, 19500, 20000, 25000, 30000, 35000, 40000, 45000, 50000, 55000, 60000, 65000, 70000, 75000, 80000, 85000, 90000, 95000 or 100000 Da. Preferably, the PEG has an average molecular weight of about between about 4500 Da to about 70000 Da. More preferably, the PEG has an average molecular weight of about 5500 Da.

In another example, conjugated hyaluronic acid can he used to enhance the delivery of ALDH2. HA is a natural linear polysaccharide composed of alternating disaccharide units of D-glucuronic acid and N-acetyl-D-glucosamine with β (1-4) interglycosidic linkage. HA is the only non-sulfated glycosaminoglycan (GAG) which is abundant in synovial fluid and extracellular matrix (ECM). HA with a high molecular weight over 2 million Da was used for the sustained release formulation of human growth hormone (Kim et al. J. Control. Rel. 104, 323-335, 2005) and selectively cross-linked HA hydrogels were used for the encapsulation of erythropoietin (Motokawa et al., J. Biomed. Mater. Res. 78A, 459-465, 2006). HA was also used for the conjugation with active cytotoxic agents, such as paclitaxel (Luo et al, Biomacromolecules 1, 208-218, 2000) and doxoruhicin (Luo et al., Pharm. Res. 19, 396-402, 2002).

In another example, the ALDH2 can be modified to be associated with larger proteins to enhance its half-life and/or activity. For example, IgG and albumin both have prolonged half-lives of 19 days compared with few days or less for other circulating proteins.

In yet another example, the structure of ALDH2 can be modified, e.g., via coupling through an amide bond with at least one conformationally rigid substituent, either at the N-terminal of the peptide, the C-terminal of the peptide, on a free amino or carboxyl group along the peptide chain, or at a plurality of these sites (see US Pub No. 2003/0204063) or via substitution of l-analogue amino acids within ALDH2 by d-amino acids.

Treatment of Acute Alcohol Poisoning

Ethanol poisoning is an acute, life-threatening toxic condition resulting from exposure to excessive quantities of ethanol within a short period of time. Administration of the ALDH2 or a composition comprising ALDH2 can be used for the treatment of alcohol poisoning, as it would help to overcome enzyme saturation and change drug metabolism from zero-order kinetics to first-order kinetics. Under first-order kinetics the amount of a drug which undergoes metabolism is proportional to the drug level rather than constant. This concept is explained in more detail below Most metabolic transformations in the body are catalyzed by enzymes and follow Michaelis-Menten kinetics. Under normal conditions, the metabolism of most drugs follows first-order Michaelis-Menten kinetics, and is directly proportional to the drug free blood concentration. However, in the case of an overdose, the metabolism changes from first-order kinetics to zero-order kinetics. Zero-order kinetics occurs because the enzymes are saturated and there are not enough of enzymes to increase drug metabolism. As a result, the amount of the drug that is metabolized over a period of time remains constant and independent from its blood concentration. See FIG. 1, a plot for a dose of ethanol, where V is the rate of drug metabolism, and $K_m$ is the Michaelis-Menten constant. At low doses metabolism of alcohol is first order, that is, proportional to drug dose. At high doses, alcohol metabolism is zero-order, constant and independent of concentration.

Ethanol is metabolized in the liver at a rate of approximately one drink per hour and large quantities of alcohol can overload the liver metabolic capacity, causing the blood alcohol concentration (BAL) to rise rapidly. The effects of ethanol on the central nervous system (CNS) are directly proportional to its blood concentration. At high BAL, CNS depression occurs and the heart and lungs become partially anesthetized possibly leading to a coma or death. At BALs of 0.25 to 0.40 g/deciliter, alcohol poisoning can lead to slurred speech, ataxia, stupor, coma and eventually death (Poikolainen K. and Vuori E. *Alcohol and Alcoholism* 20(3): 329-332. 1985).

In the general population, stupor occurs at a BAL of 0.25 to 0.40%. A coma is usually diagnosed at a BAL of 0.35 to 0.50%. All symptoms such as deepening unconsciousness, depressed reflexes, life-threatening respiratory depression and bradycardia become more pronounced at this stage. Death from ethanol consumption is possible when BAL reaches 0.4%. A BAL of 0.5% or more is usually fatal.

Ethanol poisoning occurs as a result of enzyme saturation during metabolism. Treatment with recombinant human aldehyde dehydrogenase 2 (rhALDH2) is proposed to increase the metabolism of both acetaldehyde (a toxic intermediate product) and ethanol.

Figure 2:
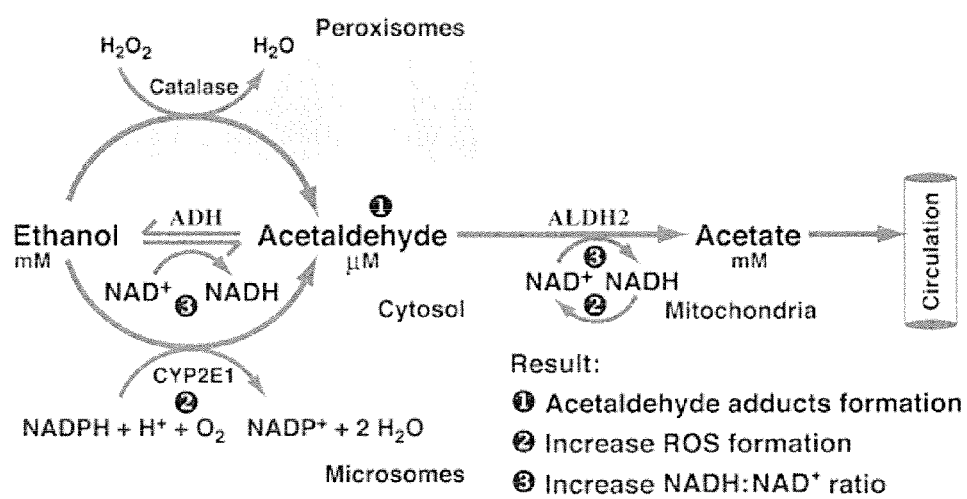
FIG. 2 is an illustration of ethanol metabolism reactions in the liver.

Most ethanol metabolism occurs in the liver cells, as the liver has the highest concentration of enzymes involved in metabolism. In the first reaction of ethanol metabolism, ethanol is oxidized to acetaldehyde via the enzyme alcohol dehydrogenase 1 (ADH1). This first reaction is reversible, and with increased acetaldehyde levels, ethanol and acetaldehyde levels reach equilibrium (FIG. 2). The same enzyme ADH metabolizes reaction in both directions. Activity of ADH is significantly higher in the reverse reaction, to avoid accumulation of toxic acetaldehyde (Umulis D M et al., *Alcohol.* 2005 January: 35 (1):3-12.

Under normal conditions, during the second reaction, acetaldehyde, a highly toxic metabolite, is rapidly metabolized by ALDH2 to form acetate. Acetate has significantly less toxic properties compared to acetaldehyde. Acetate is then metabolized in the liver and adipose tissue to form acetyl-CoA. Conversion of acetate to acetyl-CoA is not a rate-limiting reaction. With a high dose of ethanol consumption, both enzymes ADH1 and ALDH2 become saturated, leading to a significant increase of acetaldehyde and ethanol levels in the blood as well as in the liver.

When ALDH2 becomes saturated, the second metabolic reaction (conversion of acetaldehyde to acetate) becomes rate-limiting. After administration of rhALDH2, saturation of ALDH2 is lifted and first order kinetics would be reinstated, driving the reaction to the right. Removal of acetaldehyde would move the equilibrium of the first reaction toward acetaldehyde formation, and as both forward and reverse reaction use the same enzyme there would be a significant increase of amount of the enzyme available for the forward reaction. In result there will be an increase in metabolism of both ethanol and acetaldehyde. Both reactions involve an intermediate carrier of electrons, nicotinamide adenine dinucleotide ($NAD^+$), which is reduced by two electrons to form NADH. The concentration of NAD in the blood is sufficient to support increase of the second reaction in the bloodstream.

Moving the second reaction from the liver to the blood stream would make more NAD available for the first reaction.

Hence, the metabolism of toxic levels of alcohol and acetaldehyde would be cleared more rapidly to alleviate life-threatening symptoms (coma and death) of CNS depression due to intoxication. Administration of ALDH2 or a composition comprising ALDH2 would allow for the change of ethanol metabolism from zero-order to the first-order and would significantly increase the metabolism of alcohol to its final and non-toxic end product.

Use of ALDH2 for Treatment of Drug-disulfiram Reaction.

Patients who are taking disulfiram have a deficiency of ALDH2, as it is the mechanism of action for this drug. If a patient takes disulfiram and consumes alcohol they accumulate acetaldehyde and develop symptoms of acetaldehyde poisoning (or alcohol-disulfiram reaction). Fear of this reaction generally prevents people from drinking. However, acetaldehyde is significantly more toxic than ethanol and fatal acetaldehyde poisoning may occur with relatively small doses of ethanol.

Administration of ALDH2 or a composition comprising ALDH2 would help to overcome enzyme deficiency and would allow the acetaldehyde metabolism to occur in the bloodstream rather than liver cells. Exogenous administration of ALDH2 or a composition comprising ALDH2 would be a very effective treatment for alcohol-disulfiram reaction. Treatment with disulfiram becomes much safer, as the potential side effects are no longer unavoidable and likely to be lethal.

Disulfiram is also used to treat cocaine dependency because disulfiram interferes with the metabolism of cocaine by blocking the enzyme dopamine β-hydroxylase (DBH), and it shows efficacy for this indication as well. The use of ALDH2 or a composition comprising ALDH2 can also limit the toxicity when cocaine is ingested by a person taking disulfiram. Thus, the methods and compositions of the invention are useful for addiction diseases, and not limited to treatment of alcohol.

Use of ALDH2 with Controlled Release Disulfiram

The ability to limit the toxicity observed with a drug-disulfiram reactions allows the use of disulfiram with controlled release dosage formats, such as implantable devices. This enables new treatment regimens and development of a new generation of disulfiram-device combinations which delivers doses that are bioequivalent to orally administered doses used to treat alcoholism and cocaine dependencies.

Use of ALDH2 in Ischemia-reperfusion Injury

A significant amount of scientific data shows that mitochondrial ALDH2 enzyme plays a critical role in cardio protection. ALDH2 or a composition comprising ALDH2 can also be used to limit additional an ongoing damage (e.g., remodeling) that takes place in ischemic events by limiting the toxicity associated with toxic aldehydes at the time of the ischemic event.

Figure 3:
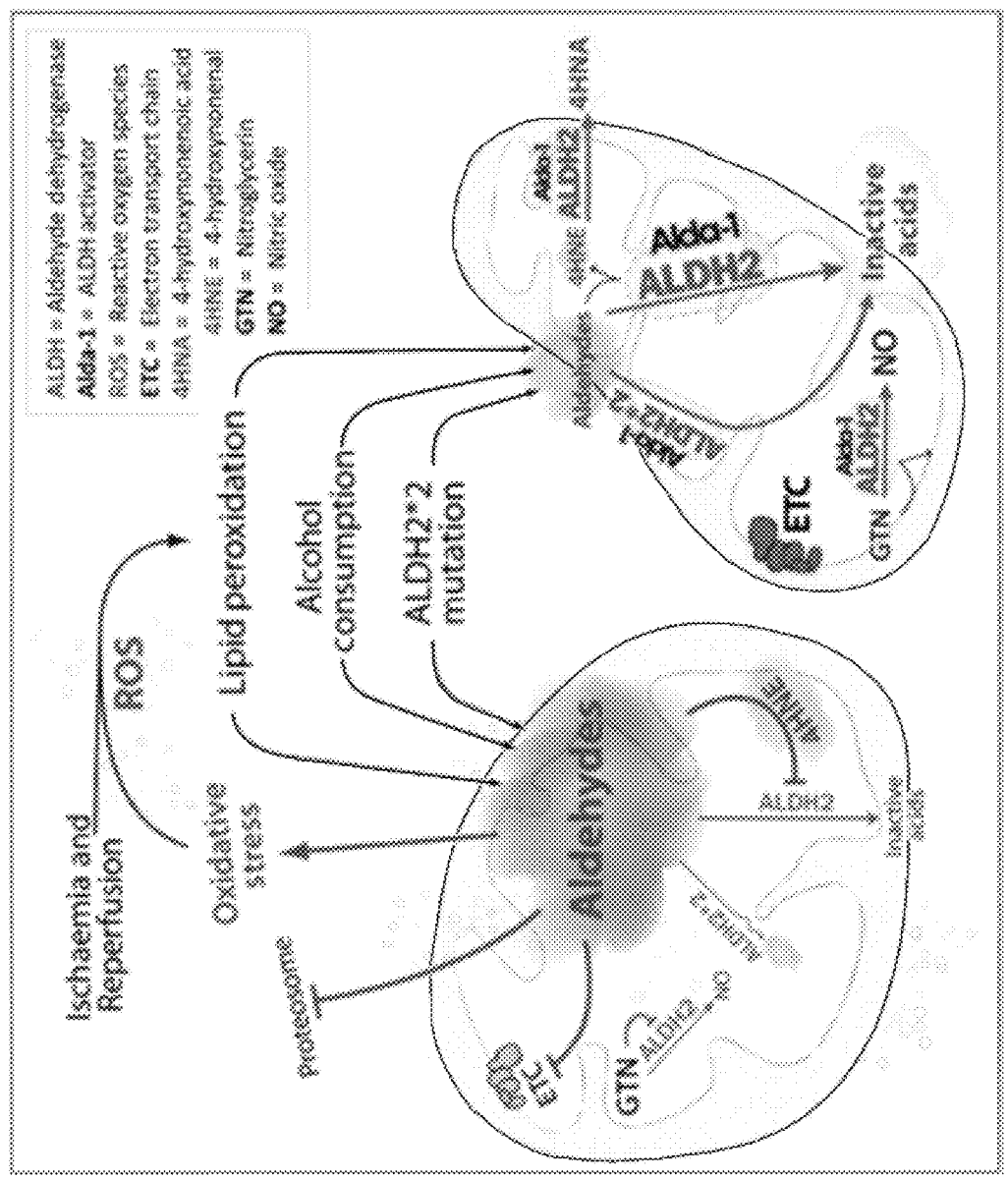
FIG. 3 is an illustration showing the pathway for toxic aldehyde formation during ischemia-reperfusion injury.

Without being limited by any particular theory, the cardio protective effect of ALDH2 can be explained at least in part by the fact that this enzyme is involved in the detoxification of reactive aldehydes which are created during ischemia-reperfusion injury caused by MI (Budas, G. et al., *Trends in Cardiovascular Medicine*, Vol. 19, Issue 5, Jul. 2009 p 158-164; Chen C-H et al. *Science* Vol 321 12 Sep. 2008 p. 1493-5.) (FIG. 3). Ischemia-reperfusion creates oxidative stress in myocardial cells and results in excessive production of reactive oxygen species (ROS) and $H_2O_2$. ROS is produced during both stages of ischemia-reperfusion injury. During the initial ischemic phase, ROS production occurs because of metabolic disarrangement despite low levels of oxygen (Ferrari R. et al., *Am. J. Of Clinical Nutrition.* 1991; 53:21S-22S.). However, when oxygen becomes abundant during reperfusion the process of ROS formation intensifies significantly. (Id.). Although ROS are short lived they are highly toxic and reactive molecules and they are causing secondary changes in myocardial cells. Elevated levels of ROS -induced stress lead to lipid peroxidation (oxidative degradation of lipids). ROS creates free radicals that "take" electrons from the cell membranes lipids resulting in cell damage. Lipid peroxidation results in production and accumulation of toxic aldehydes, most important 4-hydroxynonenal (4-HNE) and malondialdehyde (MDA). By virtue of their increased chemical stability, these lipid peroxidation-derived aldehydes diffuse greater distances compared with their precursor ROS and behave as secondary toxic messengers that can propagate and amplify oxidative injury (Srivastava S. et al., *Am. J. Physiol Heart Cure Physiol.* 283:2612-2619, 2002. First published Aug. 22, 2002).

ALDH2 is one of the most important enzymes involved in the metabolism of different aldehydes such as acetaldehyde, 4-HNE and others. ALDH2 metabolizes aldehydes to non-toxic, non reactive acids, which either relatively quickly removed from the body or enter other metabolic pathways. 4-HNE is used as a marker of radical -induced lipid peroxidation (LPO) (Blasig I. et al., *Am. J. Physiol.,* 269 (Heart Circ. Physiol. 38 H1-H22)). A study performed on the isolated heart of Wistar-Kyoto rats showed statistically significant increases in 4-HNE levels ($P<0.05$) 2 min after the onset of reperfusion (after 30 minutes of total and global ischemia) (Id). 4-HNE has many negative effects on myocardial cells, and as a cardio-toxin, 4-HNE directly inhibits contractility and induces pro-arrhythmic effects in isolated cardiac myocytes causing additional damage after cardiac ischemia (Chen C-H et al. Id.) Use of ALDH2 following an ischemic event can be useful to metabolize 4-HNE and other harmful aldehydes to prevent additional tissue damage, Inactivation of ALDH2 also reduces the effectiveness of nitroglycerin (GTN), the drug used frequently to treat angina pectoris and MI. GTN main mechanism of action is dilatation of cardiac vessels. ALDH2 mediates bioavailability of GTN by converting it into 1,2-glyceral dinitrate, the active metabolite of the drug. Decreased activity of ALDH2 may be implicated to increase tolerance (decrease response) to GTN in animals as well as humans. Decreased response to GTN may contribute to increased size of MI. GTN itself contributes to decreased activity of ALDH2 resulting in further increase of "aldehydic load" and size of MI (Chen C-H et al. Id.)

The toxic effect of endogenous aldehydes not only affect the cells were they are produced, but also adjacent myocardial cells. Aldehydes move easily through cell membranes and may cause adduct formation in other myocardial cells which are not directly affected by severe ischemia. The negative effect of aldehydes on the myocardial cells is well documented. Elevated aldehyde levels from excessive alcohol consumption play a significant role in the development of cardiac alcohol related cardiomyopathy. Environmental and dietary aldehydes may contribute to damage during MI as well (Chen C-H et al. Id.)

All these factors implicate toxic, reactive aldehydes in playing a significant role in the pathophysiology of damage caused by acute cardiac ischemia-reperfusion. Mitochondrial ALDH2 plays a significant role in cardio protection by decreasing oxidative stress and by reducing the "aldehydic load" to the myocardial cells (Chen, 2008).

Administration of ALDH2 or a composition comprising ALDH2 during or immediately after the ischemic event can limit the additional damage done by these aldehydes. ALDH2 administration will decrease "aldehydic load" in interstitial fluid, resulting in diffusion of toxic aldehydes from the myocardial cells into interstitial fluid, based on the concentration gradient. It will also decrease aldehyde load from dying myocardial cells to adjacent myocardial cells, and improve survival of cells only partially affected by ischemia.

Administration

Administration of a compound of the invention may be accomplished by any convenient means, including parenteral and controlled release administration. ALDH2 can be incorporated into a variety of formulations for therapeutic administration, including by combining the ALDH2 with appropriate pharmaceutically acceptable carriers Unit dosage forms for injection or intravenous administration may comprise ALDH2 in a composition as a solution in sterile water, normal saline or another pharmaceutically acceptable carrier. It also may be formulated in a composition with other active agents.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host.

Dosage

Depending on the patient and condition being treated and on the administration route, the compositions of the invention will generally be administered as a therapeutically effective dosage of from 0.001 g per kg body weight to 5 g per kg body weight. More preferably, the compositions of the invention will generally be administered as a therapeutically effective dosage of from 0.1 g per kg body weight to 2 g per kg body weight. Higher doses may be used for localized routes of delivery.

In a subject under the influence of a pharmacologically active substance, the amount of ALDH2 or a composition comprising ALDH2 that is administered is sufficient to result in a measurable decrease in the systemic levels of at least one toxic aldehyde in the subject's bloodstream, and preferably a measurable decrease in two or more toxic aldehydes in the subject's bloodstream. The measurable decrease of toxic aldehydes can is from 5-99%, more preferably the at least a 10% decrease in the systemic levels of toxic aldehydes in the subject's bloodstream, more preferably at least a 20% decrease in the systemic levels of toxic aldehydes in the bloodstream, more preferably at least a 30% decrease in the systemic levels of toxic aldehydes in the bloodstream, more preferably at least a 40% decrease in the systemic levels of toxic aldehydes in the bloodstream, and more preferably at least a 50% decrease in the systemic levels of toxic aldehydes in the bloodstream.

Preferably, in a subject under the influence of a pharmacologically active substance, the amount of ALDH2 or a composition comprising ALDH2 that is administered is sufficient to restore first order kinetics of the pharmacologically active substance.

In a subject that is undergoing or has undergone an ischemic event, the amount of ALDH2 or a composition comprising ALDH2 that is administered is also sufficient to result in a measurable decrease of size of MI or ischemic damage to other organs.

A typical dosage may be: a solution suitable for intravenous administration; a depot injection; a time-release device such as an osmotic pump, or by any other known means of controlled release. Those of skill will readily appreciate that dose levels can vary as the severity of the symptoms and the susceptibility of the subject to side effects. Preferably. the ALDH2 or composition comprising ALDH2 is administered in a level that will return the level of the toxicity to a level not associated with pathology. As this amount will vary according to the amount of a drug ingested or the level of injury sustained, it should be adjusted by the medical practitioner.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Example 1

Intrapeitoneal Administration of ALDH

Figure 4:
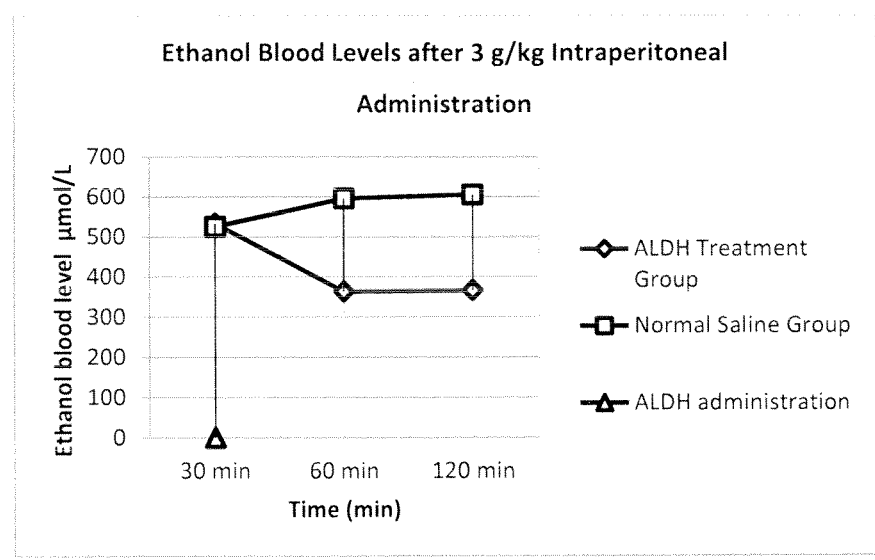
FIG. 4 is a graph illustrating the effects of intraperitoneal ALDH administration following ethanol administration in a rat model.

16 Sprague Dawley male rats (weight 275-330 g) were divided into an active treatment group and a placebo group, each group composed of eight animals. Both the active and placebo groups received a 20% ethanol solution, which was administered via intraperitoneal injection. After administration of ethanol, ethanol levels were collected at three time points: Point 0 at 30 minutes following ethanol administration. Point 1 at 1 hour following ethanol administration, and Point 3 at 2 hours following ethanol administration (FIG. 4). The treatment group received the 300 U/saline 200 µL ALDH enzyme solution at Point 0 or 30 minutes after the administration of ethanol. The control group received an equal amount of the normal saline IV at the same time points. One unit of enzyme was defined as the amount of the enzyme that catalyzes the conversion of one micromole of NAD to NADH at pH 8.0 when at room temperature. For each animal the dose of the ALDH enzyme was calculated based on its most recent body weight. As shown in FIG. 4, prior to administration of the enzyme, there was not a statistically significant difference observed between the control and treatments groups. The levels were 533±25.5 and 525 µmol/L±31 in treatment and control groups respectively. 30 minutes after administration of the ethanol enzyme (or 1 h after the administration of ethanol) the blood ethanol levels were 363±23.4 in the treatment group and 595 µmol/L±16.9 in the control group, which is statistically significant ($P<0.005$). 120 minutes after administration of ethanol (point 3) ethanol levels were 366.4±30.5 and 605 µmol/L±28.4 also statistically significant. ($P<0.05$))

What is claimed is:

1. A method of treating toxicity associated with an ALDH2 deficiency in a subject, comprising administering ALDH2 or a composition comprising ALDH2 to the subject having an ALDH2 deficiency in a therapeutically effective dosage to at least partially reduce the toxicity; wherein the therapeutically effective dosage is from 0.001 g per kg body weight to 5 g per kg body weight.

2. The method of claim 1, wherein the ALDH2 is modified ALDH2.

3. The method of claim 2, wherein the ALDH2 is PEGylated.

4. The method of claim 1, wherein the subject has a temporary ALDH2 deficiency.

5. The method of claim 1, wherein the subject is under the influence of a pharmacologically active substance.

6. The method of claim 5, wherein the pharmacologically active substance is alcohol.

7. The method of claim 5, wherein the pharmacologically active substance is cocaine.

8. The method of claim 1, wherein disulfiram has been administered to the subject.

9. The method of claim 1, wherein the ALDH2 deficiency is a genetic ALDH2 deficiency.

10. The method of claim 1, wherein the therapeutically effective dosage is from 0.1 g per kg body weight to 2 g per kg body weight.

11. The method of claim 1, wherein the dosage is adapted to provide at least a 35% reduction of the systemic level of toxic chemicals in the subject.

12. The method of claim 1, wherein the dosage results in at least a 50% reduction of the systemic level of toxic chemicals in the subject.

13. The method of claim 1, wherein the administration is used as an adjunctive therapy to disulfiram administration.

14. The method of claim 13, wherein the disulfiram is delivered using a controlled release dosage format.

15. The method of claim 14, wherein the controlled release dosage format is an implantable device.

16. The method of claim 1, wherein said administration of ALDH2 is by parenteral injection.

17. The method of claim 1, wherein the ALDH2 deficiency comprises ALDH2 enzyme saturation with alcohol in the subject.

18. The method of claim 17, wherein said administering further comprises administering adequate ALDH2 to provide first-order alcohol metabolism kinetics in the subject.

19. The method of claim 8, wherein said administration of disulfiram is by a controlled release implant.

20. The method of claim 8, wherein the subject has consumed alcohol and is experiencing an alcohol-disulfiram reaction.

* * * * *